(12) United States Patent
Tesi et al.

(10) Patent No.: US 10,758,567 B2
(45) Date of Patent: Sep. 1, 2020

(54) IN VIVO PRIMING OF NATURAL KILLER CELLS

(71) Applicant: Immune Ventures LLC, Seattle, WA (US)

(72) Inventors: Raymond J. Tesi, Seattle, WA (US); David Moss, Seattle, WA (US)

(73) Assignee: Immune Ventures LLC, Seattle, WA (US)

( * ) Notice: Subject to any disclaimer, the term of this patent is extended or adjusted under 35 U.S.C. 154(b) by 0 days.

(21) Appl. No.: 15/268,399

(22) Filed: Sep. 16, 2016

(65) Prior Publication Data
US 2017/0071982 A1 Mar. 16, 2017

Related U.S. Application Data

(60) Provisional application No. 62/263,951, filed on Dec. 7, 2015, provisional application No. 62/219,652, filed on Sep. 16, 2015.

(51) Int. Cl.
A61K 35/13 (2015.01)
A61P 35/00 (2006.01)
A61K 41/10 (2020.01)
C12N 5/0783 (2010.01)

(52) U.S. Cl.
CPC .............. A61K 35/13 (2013.01); A61K 41/10 (2020.01); A61P 35/00 (2018.01); C12N 5/0646 (2013.01); C12N 2501/2302 (2013.01); C12N 2501/2315 (2013.01); C12N 2502/30 (2013.01)

(58) Field of Classification Search
CPC ... C12N 5/0646; A61K 35/13; A61K 41/0009
USPC ........................................................ 435/325
See application file for complete search history.

(56) References Cited

U.S. PATENT DOCUMENTS

| | | |
|---|---|---|
| 8,034,332 B2 | 10/2011 | Klingemann |
| 8,257,970 B2 | 9/2012 | Lowdell |
| 8,637,308 B2 | 1/2014 | Lowdell |
| 8,735,148 B2 | 5/2014 | Lowdell |
| 2002/0068044 A1 | 6/2002 | Klingemann |
| 2004/0018182 A1 | 1/2004 | Klingemann |
| 2004/0018183 A1 | 1/2004 | Klingemann |
| 2004/0022773 A1 | 2/2004 | Klingemann |
| 2004/0052770 A1 | 3/2004 | Klingemann |
| 2006/0019256 A1* | 1/2006 | Clarke ................. C12N 5/0695 435/6.14 |
| 2006/0110360 A1 | 5/2006 | Klingemann |
| 2014/0079678 A1 | 3/2014 | Lowdell |
| 2014/0099714 A1 | 4/2014 | Klingemann |

FOREIGN PATENT DOCUMENTS

WO 2013175237 11/2013

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Drexler et al (Leukemia and Lymphoma, 1993, 9:1-25).*
Zellner et al (Clin. Can. Res., 1998, 4:1797-1802).*
Zips et al (In vivo, 2005, 19:1-7).*
Gura (Science. 1997; 278: 1041-1042).*
Dennis (Nature. Aug. 7, 2006; 442: 739-741).*
Ishii et al. (Cancer Immunol Immunother, 2004, 53: 383-390).*
North et al., Tumor-Primed Human Natural Killer Cells Lyse NK-Resistant Tumor Targets: Evidence of a Two-Stage Process in Resting NK Cell Activation, J. Immunology, 2007, 178:85-94.
Carlstein et al., Primary Human Tumor Cells Expressing CD155 Impair Tumor Targeting by Down-Regulating DNAM-1 on NK Cells, J. Immunology, 2009, 183: 4921-4930.
Katodritou, Tumor-primed natural killer cells from patients with multiple myeloma lyse autologous, NK-resistant, bone marrow-derived malignant plasma cells, Am. J. Hematol. 2011, 86: 967-973.
Danylesko et al., Novel Strategies for Immunotherapy in Multiple Myeloma: Previous Experience and Future Directions, Clinical and Developmental Immunology, 2012, vol. 2012, Article ID 753407, 28 pages.
Ayala-Breton et al., Biological Therapy for Multiple Myeloma, 2014.
Bruno et al., A Think Tank of TINK/TANKs: Tumor-Infiltrating/ Tumor-Associated Natural Killer Cells in Tumor Progression and Angiogenesis, Oxford University Press, Sep. 1, 2014, vol. 106, Issue 8, 13 pgs.
Mortara et al., Polarization of Tumor Infiltrating Leukocytes from Innate Immunity and their role in the Pro-angiogenic Phenotype in NSCLC, J Clin Cell Immunol 2015, 6:2.
Koehl, U. et al., Advances in clinical NK cell studies: Donor selection, manufacturing and quality control, OncoImmunology, 2016, 5:4.
Lowdell et al., Tumor-Activated Human NK Cells Specifically lyse Autologous and Allogeneic NK-Resistant Tumor Targets, Blood 2006 108:3707.

(Continued)

Primary Examiner — Yan Xiao
(74) Attorney, Agent, or Firm — Coastal Patent Law Group, P.C.

(57) ABSTRACT

The disclosure concerns a method for cancer treatment by in vivo priming and activation of natural killer cells for achieving tumor cell lysis. The method includes introducing into a patient a priming tumor cell preparation (PTCP) derived from a first tumor cell line, which is irradiated to inactivate the first tumor cells or a membrane preparation thereof, the first tumor cells having known priming ligands on the membrane surface thereof. The patient's rest NK cells are contacted by the PTCP in vivo, resulting in primed NK cells, which are characterized by upregulation of CD69, shedding of CD16, or a combination of CD69+ and CD16-. These primed NK cells then contact second tumor cells, the cancer, and are configured to lyse and kill the second tumor cells.

2 Claims, 4 Drawing Sheets

(56) References Cited

OTHER PUBLICATIONS

Rosenberg, et al., "A progress report on the treatment of 157 patients with advanced cancer using lymphokine-activated killer cells and interleukin-2 or high-dose interleukin-2 alone," N. Engl. J. Med, 3161889-897 (1987).

Miller, et al., "Low dose subcutaneous interleukin-2 after autologous transplantation generates sustained in vivo natural killer cell activity," Biol. Blood Marrow Transplant, 3:34-44 (1997).

North, J., et al., "Tumor-primed human natural killer cells lyse NK resistant tumor targets: evidence of a two-stage process in resting NK cell activation," J. Immunol., 178(1)185-94 (2007).

Sabry et al., Tumor-primed NK cells: waiting for the green light, Frontiers in immunology, Nov. 25, 2013, vol. 4, Article 408.

Kottaridis et al., Two-Stage Priming of Allogeneic Natural Killer Cells for the Treatment of Patients with Acute Myeloid Leukemia: A Phase I Trial, PLoS ONE, 2015, 10(6): e0123416.

Sabry et al., Leukemic Priming of Resting NK Cells Is Killer Ig-like Receptor Independent but Requires CD15-Mediated CD2 Ligation and Natural Cytotoxicity Receptors, J. Immunol. 2011; 187:6227-6234.

Bryceson, Yenan T. et al "Synergy among receptors on resting NK cells for the activation of natural cytotoxicity and cytokine secretion." Blood 107.1 (2006): 159-166 Web. Mar. 25, 2019.

\* cited by examiner

```
┌─────────────────────────────────────────┐
│   Obtaining pharmaceutical grade CTV-1 cells │
└─────────────────────────────────────────┘
                    │
                    ▼
┌─────────────────────────────────────────────────┐
│  Optinally modifying the CTV-1 cells to knock-in │
│  and/or Knock-out HLA class I or class II antigens│
│       using known genetic modification techniques │
└─────────────────────────────────────────────────┘
                    │
                    ▼
       ┌──────────────────────────┐
       │ Inactivating the CTV-1 cells │
       └──────────────────────────┘
                    │
                    ▼
       ┌──────────────────────────────┐
       │ Introducing the inactivated CTV-1 cells into │
       │              a patient        │
       └──────────────────────────────┘
                    │
                    ▼
┌──────────────────────────────────────────────────┐
│ contacting rNK cells with the inactivated CTV-1 cells *in vivo* │
│       to form non-naturally occuring pNK cells    │
└──────────────────────────────────────────────────┘
                    │
                    ▼
       ┌──────────────────────────────┐
       │ wherein the pNK cells are enhanced │
       │        for tumor cell killing │
       └──────────────────────────────┘
```

*FIG.1*

A method for treating cancer, comprising:

administering to a patient having said cancer a priming tumor cell preparation for priming natural killer cells of the patient *in vivo*, the priming tumor cell preparation including cells and/or membrane portions derived from a CTV-1 myeloid leukemia cell line, wherein the priming tumor cell preparation is inactivated to prevent proliferation thereof in the patient; whereby said patient is treated.

OPTIONALLY: wherein the priming tumor cell preparation is irradiated to achieve inactivation.

FIG.4

IN VIVO PRIMING OF NATURAL KILLER CELLS

CROSS-REFERENCE TO RELATED APPLICATIONS

This application claims benefit of priority with U.S. Provisional Ser. No. 62/263,951, filed Dec. 7, 2015; and also claims benefit of priority with U.S. Provisional Ser. No. 62/219,652, filed Sep. 16, 2015;

the contents of each of which are hereby incorporated by reference.

BACKGROUND

Field of the Invention

This invention relates to methods for cancer treatment; and more particularly, in vivo priming of natural killer cells for the treatment of cancer and other diseases.

Description of the Related Art

A natural killer (NK) cell is a lymphocyte able to bind to certain tumor cells and virus-infected cells without the stimulation of antigens, and kill them by the insertion of granules containing perforin.

Many cancers develop and proliferate in the body because NK cells are unable to recognize and engage them for lysing. The first is a failure of immune surveillance. The latter is due changes on the tumor that allow it to evade NK cell killing.

U.S. Pat. No. 8,257,970, issued Sep. 4, 2012, describes a method for activating natural killer cells by tumor cell preparation in vitro; the contents of which are hereby incorporated by reference. While the embodiments of the '970 patent seem to be promising, there are many problems associated with applying the technology in a commercial platform, such as, inter alia, scalability and broad application to unique patients and diseases.

Indeed, the problem of finding effective methods for treating cancer is long felt and largely unresolved. For this reason, the United States government has launched a program coined "Cancer Moonshot"; which in essence seeks to double the rate of progress toward a cure, or to make a decade worth of advances in five years.

There is a continued need for novel methods to stimulate an immune response for the purpose of treating cancer and other diseases.

SUMMARY

A method is disclosed for treating various cancers in human and animal patients. The problem with many cancers is that the cancer cells downregulate certain signals on the membrane surface, effectively evading NK cell killing. Herein described is a strategy and method for "priming" the NK cells in vivo such that they are exposed to those signals which are often downregulated on the tumor cell, then, upon contacting the tumor cell, the NK cells are capable of activation by contact with the remaining signals which are not down regulated on the tumor cell surface, thereby promoting tumor cell lysis. In sum, the method achieves "priming" of Natural Killer (NK) cells in vivo, wherein resting NK (rNK) cells become primed NK (pNK) cells upon contact with a priming tumor cell preparation (PTCP). The primed NK cells are then capable of complete activation and tumor cell lysis upon contacting the tumor cells and remaining signals.

BRIEF DESCRIPTION OF THE DRAWINGS

FIG. 1 illustrates a method for in vivo priming of NK cells in accordance with an illustrated embodiment.

FIG. 4 shows a method of treating cancer according to an embodiment.

DETAILED DESCRIPTION OF PREFERRED EMBODIMENTS

Figure 2B:
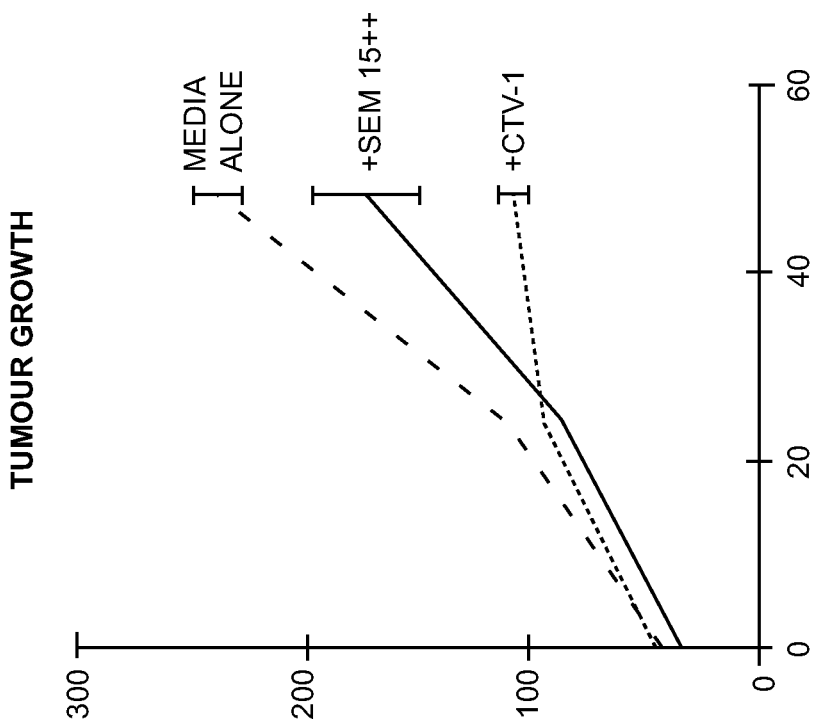
FIG. 2B shows that growth of RAJI cells, a NK resistant tumor line, when added to a population of human PBMC is significantly decreased if CTV1 cells are added to the culture.

Tumor killing using natural killer (NK) cells is a two-step process that involves priming and triggering; i.e. the NK cell must be primed and triggered to cause killing of a tumor cell. Priming and triggering are each controlled by a different set of receptors and ligands on the NK cell and the tumor cell, respectively. The majority of naturally occurring human cancers are resistant to NK killing because they lack the priming ligands on their cell surface. That is, the triggering ligands remain on the tumor cell surface, but the NK cell does not cause tumor cell death because it does not become primed (i.e., there are no priming ligands on the tumor cell surface). Due to the lack of priming ligands (hereinafter "Signal 1") on the tumor cell surface, at least with respect to the vast majority of human cancers, NK cells do not and cannot participate in the control of cancer growth in patients. Herein is disclosed a strategy to artificially "prime" NK cells so they will be capable of killing (lysing) a tumor cell, that is, when the primed NK cells come in contact with a triggering signal (hereinafter "Signal 2") that is on the surface of the tumor cell. The technologies disclosed herein will increase the role human NK cells play in the control of human cancer—both prevention and treatment.

The role of NK cells in the control of cancer was first described using cytokines to prime NK cells. The discovery of interleukin-2 (IL-2) and its role in NK-cell activation in the 1980's led to considerable interest in the use of lymphokine-activated killer (LAK) cells in tumor immunotherapy. The results of these trials were, however, largely disappointing. In a study investigating the effect of administering autologous LAK cells to patients along with IL-2, fewer than 20% of patients responded (Rosenburg et al.). Subsequent studies have shown that IL-2 significantly expands the number of circulating NK cells in vivo, but the cells are not maximally cytotoxic (Miller et al.).

More recently, a cytokine free priming technique has been developed that uses carefully selected tumor cells that have retained the priming ligands, but lack the triggering ligands (North et al.). When resting NK cells (rNK cells are CD69−) are placed with priming tumor cells (PTC), for example, CTV-1 cells, NK cells become primed as defined by the activated phenotype (pNK cells are CD69+) and by shedding CD16. pNK cells will kill tumor cells that have triggering ligands on their cell surface. This is believed to be true, and in some instances, confirmed, in many human tumor types, including but not limited to: myeloid leukemia, multiple myeloma, chronic myeloid leukemia, lymphoma, breast, ovary, lung, renal, prostate and other GI and GYN malignancies. That is, in a vast majority of patients, their tumors evade NK cell killing by eliminating priming ligands on their cell surface, but are still susceptible to killing by primed NK cells because they retain trigger ligands on their cell surface.

Tumors are either resistant to NK cell killing (NK resistant) or are killed by NK cells (NK sensitive). A vast majority of tumors and tumor cell lines are NK resistant. Most NK resistant tumors and cell lines do not have priming ligands on their cell surface yet do express triggering ligands. This means the NK cell does not receive one of the two signals needed for it to kill the tumor cell. Because NK resistant tumors still have the triggering ligands on their cell surface, they will be killed by NK cells that have received a priming signal; as evidenced by the susceptibility of these NK-resistant lines to NK cells primed by IL-2 which provides a priming signal. IL-2 is a highly potent cytokine which has proved difficult to use clinically because the high dose needed to induce systemic NK cell priming also causes severe and often fatal side effects. Thus, it has been discovered and is indeed a strategy as disclosed herein, to artificially provide the priming signal in vivo to convert rNK cells to pNK cells that will be able to interact and kill tumor cells without administration of toxic levels of cytokines.

A resting NK cell that has received the priming signal (Signal 1) as part of the therapy is called a Tumor Primed NK cell (TpNK). TpNK sensitive tumors are the majority of hematologic and solid tumors. However, there are TpNK resistant cancers; for example chronic lymphocytic leukemia (CLL). These rare TpNK resistant tumors will not be eligible for treatment by this in vivo priming therapeutic strategy.

The rare cancer and cancer cell lines that retain priming ligands (Signal 1) on their cells surface yet lack the triggering signals are herein termed "NK priming tumor cells (PTC)". PTC's evade NK cell killing by downregulating triggering ligands (S2) from their cell surface—they are the mirror image of the vast majority of cancers that evade NK cell killing by eliminating priming ligands (Signal 1) on their cell surface. PTC are a small, but identifiable subset of tumor cells that have some combination of at least three priming ligands which cause ligation of the NK receptors CD2, LFA-1, NKp46, 2B4 and DNAM-1 expressed on their cell surface. CTV-1 cells, a cell line derived from a patient with acute lymphoblastic leukemia, expressing priming ligands, such as CD15, CD18/11a and others, on their surface, and lysates thereof, will prime human resting NK cells. It has been discovered that tumor cells expressing ligands of NKp46, 2B4 and DNAM on their cell surface can be used to prime resting human NK cells. It is further contemplated that other combinations of CD2, LFA-1, NKp46, 2B4 and DNAM receptors can be used to prime human NK cells.

Priming of resting NK cells can occur in vitro and/or in vivo. In vitro priming, although effective, is logistically complex, costly and limiting as a therapy for cancer. In this document, in vivo priming of NK cells is disclosed, where the patient's resting NK cells are primed without leaving the circulation.

Some cancers, which have down regulated the triggering ligand (Signal 2) from their cell surface will be resistant to TpNKs. When a TpNK comes in contact with a TpNK resistant tumor (TRT), only priming signals (Signal 1) are provided and, without triggering signal (Signal 2), the TpNK cell is not triggered and the tumor is not killed. TRT's will require a different therapeutic strategy.

PTCP for In Vivo Priming of NK Cells

A priming tumor cell preparation (PTCP) is introduced to a patient, wherein the PTCP is configured to change NK cells from a rest state, rNK cells (CD69−), to a primed state, pNK cells in vivo. Primed NK (pNK) cells are generally characterized as CD69+, CD16−, or a combination of CD69+ and CD16−. The PTCP can be delivered by intravenous, subcutaneous, intramuscular, intraperitoneal, intrathecal infusion or as an intra-nasal, trans-bronchial or conjunctival instillation. The PTCP can be a cell or portion thereof including a lysate, a fraction of the lysate, exosomes or microvesicles. The cell or portion thereof can be from a cell line that contains at least three of the priming ligands of CD2, LFA-1, NKp46, 2B4 and DNAM receptors. The cells or portion thereof can be living, irradiated, frozen, lyophilized, fixed, chemically altered or genetically altered, or otherwise provided. One embodiment includes direct injection of an irradiated tumor cell line with three or more of the priming ligands described above. Another embodiment is injection of a tumor cell lysate, or portion thereof, to convert rNK cells to pNK cells. The PTCP can be a manmade product including antibodies (monoclonal, bi and tri-specific antibodies and minibodies), proteins, aptamers, small molecules or combinations that will present priming ligands to rNK cells and convert them to pNK cells. One embodiment is the injection of two bispecific antibodies that bind the targets of the priming ligands. Another embodiment is to inject a tri-specific antibody that binds the targets of the priming ligands. The PTCP can be a combination product of cells and manmade products. For instance, a man-made sphere can be coated with a lysate of a tumor cell line to produce a PTCP. The PTCP can be a combination of man-made products. In one embodiment, a nanosphere of lipids, metals, polymers or combinations, is coated with antibodies the bind the targets of the priming ligands. In another embodiment, a nanosphere of lipids, silanes, polymers or combinations, is coated with synthetic priming ligands, aptamers or proteins the bind the targets of the priming ligands.

The priming tumor cell preparation (PTCP) can be given as a single therapy, a continuous therapy or a combination of single and continuous treatments. The PTCP can be given once a day, or every day. The PTCP can be used once or multiple times. The PTCP can be given as part of combination therapy with other drug, radiation and surgical therapies.

In some embodiments, where the PTCP is a whole cell, several unique characteristics can be designed into the PTCP using genetic engineering techniques such as, but not limited to, gene editing DNA nuclease based techniques including, inter alia, zinc fingers, CRISPR or TALEN, viral vector based gene editing with rAAV or other viral vectors and other genetic engineering methods. Because whole cell PTCP stimulates the immune response of the patient, genetic modification of the whole cell based PTCP to decrease the immune response of the patient to the allogeneic cell can be performed. In one embodiment, the expression of HLA Class I antigens from the cell surface is eliminated. In another embodiment, HLA Class I and HLA Class II antigens are eliminated from the surface of the cell. In another embodiment, there is an increase in surface protein expression that protects the cell from immunologic attack such as increase HLA E expression and/or increased HLA G expression. These genetic modifications of the PTCP will increase the utility of a whole cell based PTCP by decreasing and/or eliminating the need to use concomitant immunosuppression in the patient and facilitate multiple treatments of the patient using the cell based PTCP.

In embodiments where the PTCP is a living whole cell, there is potential for the cell to proliferate or engraft (take up semi-permanent or permanent residence in the patient). Where proliferation or engraftment is not desired, techniques to prevent live cell proliferation can be designed into the treatment protocol or into the cell. In one embodiment, the living whole cell PTCP is irradiated before infusion into the patient so the cells do not proliferate. Irradiation will also prevent engraftment of the live, whole cell PTCP. In another embodiment, the cells are treated with a cytotoxic agent before infusion into or exposure to the patient. In another embodiment, the cells are lyophilized before infusion into the patient. Lyophilization prevents further cell division. In another embodiment, the cells are genetically modified to include a suicide gene such as, but not limited to, thymidine kinase. In a live whole cell PTCP, genetically engineered to include a suicide gene, the drug that triggers the suicide gene to kill the living whole cell PTCP is given to the patient when you want to eliminate the NK cell priming effects of the live whole cell PTCP in the patient. For example, in the case of the thymidine kinase suicide gene, the drug that triggers the suicide of the living whole cell PTCP that has been genetically engineered is ganciclovir. The suicide inducing drug can be administered hours, days, weeks, months or never, depending on the desired therapeutic effect, the disease burden, the patient's health and other factors. For instance, in a patient with minimal residual disease, a live whole cell PTCP may be wanted for a short course of therapy, for example once a month for one, two or three months. For patients with a greater disease burden such as metastasis to the lung or brain, a more prolonged NK priming therapy may be desired to control the disease, for example weekly, biweekly or monthly treatment for prolonged periods of time, for example 6, 12 or 18 months. For patients with disease that is controlled but not eradicated, it may be necessary to give long-term chronic therapy on a weekly, bi-weekly, monthly, bi-monthly, quarterly, semi-annually or annual fashion to control the disease and prolong survival. For any of the previous scenarios, the dose of the PTCP (otherwise termed "priming tumor cell preparation (PTCP)" and the interval between treatment may be different based on the type of tumor, the severity of the disease or the type of response. For instance, the therapy may be given a one dose monthly for 3 months, then as a maintenance therapy at half the dose every two months for the life of the patient.

The PTCP produces the pNK cell, a cell that is non-naturally occurring, and not seen in humans or animals. The NK cell merely exists in either in the resting NK cell, unable to kill cancer or virally infected cells, without ligation of either Signal 1 or Signal 2, or is an activated NK cell, that can kill cancer or virally infected cells after ligation of both S1 and S2. This invention produces an unnatural primed pNK cell that has ligation on only Signal 1 receptors. With ligation of Signal 1, the pNK has a distinct biology from resting and activated NK cells that can be measured with a combination of one or more sophisticated assays including, but not limited to, genomic, proteomic, lipidomic, metabolomics, secretomic, phenotypic and functional assays.

Thus, in a general embodiment, a method for priming NK cells comprises the step of contacting the NK cells in vivo with a priming tumor cell preparation (PTCP).

In one embodiment, the PTCP comprises irradiated intact tumor cells. The intact tumor cells may comprise on a surface thereof at least one priming ligand for causing ligation of the receptors selected from the group consisting of: CD2, LFA-1, NKp46, 2B4 and DNAM-1.

In another embodiment, the PTCP comprises an irradiated cell membrane preparation. Membranes of the cell membrane preparation may comprise at least one ligand for causing ligation of the receptors selected from the group consisting of: CD2, LFA-1, NKp46, 2B4 and DNAM.

In some embodiments, the PTCP comprises irradiated CTV-1 myeloid leukemia cells, or a membrane preparation thereof.

In some embodiments, during priming, expression of CD69 is upregulated on the NK cells. In other embodiments CD16 is shed on the NK cell surface, such that the primed NK cell is CD16−.

In another embodiment, a method for in vivo priming of NK cells, comprises: (i) introducing into a patient a PTCP comprising an irradiated tumor cell or membrane preparation thereof having one or more priming ligands attached to a membrane surface, each of said one or more priming ligands being independently capable of ligation of the receptors selected from the group consisting of: CD2, LFA-1, NKp46, 2B4 and DNAM; and (ii) contacting the NK cells in vivo with the PTCP. The method may further comprise the step of, prior to irradiating, immobilizing the tumor cell or membrane preparation in an amorphous carbohydrate-glass matrix, and irradiating the carbohydrate glass matrix with the tumor cell or membrane preparation immobilized therein. In some embodiments, the method further comprises dissolving the carbohydrate glass matrix with the tumor cell or membrane preparation immobilized therein using a solvent, for example, water. In other embodiments, the method further comprises the step of, prior to irradiation, lyophilizing the tumor cell or membrane preparation, and subsequently irradiating the lyophilized tumor cell or membrane preparation.

While irradiation can sufficiently inactivate the priming tumor cell preparation to prevent proliferation in the human body, other means can be implemented to prevent such proliferation as described herein and/or as generally known in the art.

Irradiated CTV-1 Cells for In Vivo Priming of NK Cells

Now, in a first preferred embodiment, CTV-1 cells are irradiated to form a priming tumor cell preparation (PTCP) for in vivo priming of NK cells. Optionally, genetic modifications can be implemented as described above to yield the PTCP.

While irradiation generally inactivates the tumor cells for preventing proliferation within the body, the same irradiation can harm proteins and other biomolecules associated with the tumor cells, in particular when the tumor cells are irradiated while suspended in an aqueous solution. To protect the cellular sub-components, it may be preferred to first immobilize the tumor cell preparation in an amorphous carbohydrate-glass state using methods known in the art, and subsequently irradiate the immobilized preparation. Subsequently, water can be used to dissolve the carbohydrate, and the irradiated tumor cells or portions thereof can be separated.

Alternatively, the tumor cell preparation can be lyophilized and subsequently irradiated.

In some embodiments, irradiation is not required, that is, where other means are implemented to render the PTCP unable to proliferate in the body of the patient for which it is introduced.

The CTV-1 cells express CD2, NKp46, LFA-1 ligands on their surface, which are useful to prime these receptors of the NK cells. Thus, a properly inactivated CTV-1 cell, will be safe to introduce within the human patient and will function to prime NK cells in the body.

Example 1: RAJI Lysis in Co-Culture

RAJI cells are known to be an NK cell resistant tumor cell line.

In a first experiment, human peripheral blood mononuclear cells (PBMC) were isolated from normal volunteers and cultured with RAJI cells. The PTCP for NK cell priming is added to a co-culture of PBMC with RAJI cells to modify the response of the NK cells in the PBMC to the RAJI cells in a system that mimics the naturally occurring situation of human blood in vivo. Over the period of co-incubation, an increase in RAJI cells number demonstrates the normal growth characteristics of the RAJI cell in culture. A decrease in RAJI cells in the presence of NK cells relative to the RAJI cells alone reflects RAJI cell killing (lysis) by the NK cells in the PBMC culture. The presence of the priming composition is predicted to increase the degree of RAJI cell killing by the NK cells within the PBMC population.

In a first isolate, an amount of the PBMC were spiked with a known amount of RAJI cells. In a second isolate, the same amount of PBMC were spiked with the same amount of RAJI cells and SEM 15++. In a third isolate, the same amount of PBMC were spiked with the same amount of RAJI cells and CTV-1. In a fourth isolate, the same amount of PBMC were spiked with RAJI cells and a combination of the SEM 15++ and CTV-1. The number of killed RAJI per volume was determined at time intervals of twenty-four and forty-eight hours as shown in the chart of FIG. 2A and the plot of FIG. 2B. The results indicate that SEM15++ did not reduce the proliferation of RAJI, and that CTV-1 alone, and in combination with SEM 15++, did reduce the proliferation of RAJI cells. This experiment has been repeated with different PBMC donors and the results are confirmed. From this experiment we show that CTV-1 functions to reduce the proliferation of RAJI cells. Our hypothesis is that ligands expressed on the CTV-1 cell surface function provide Signal 1 to prime the NK cells from the peripheral blood, which enables the NK cells which are now primed to kill the RAJI cells. This priming occurs in the presence of other mononuclear cells and in the presence of tumor cells that are all present.

FIG. 2A shows only the addition of CTV1 cells, a tumor cell line that expresses Signal 1 and can prime NK cells (convert rNK to pNK) can decrease the growth of RAJI cells, a NK resistant cell line, in a human (PBMC) culture. When CD15 positive SEM cells are added to the PBMC culture (as a negative control), the growth of RAJI cells is not changed, and may be increased, compared to media alone. When both CTV1 and CD15 positive SEM cells are added to the culture, there response is equivalent to the addition of CTV1 cells alone.

Figure 2A:
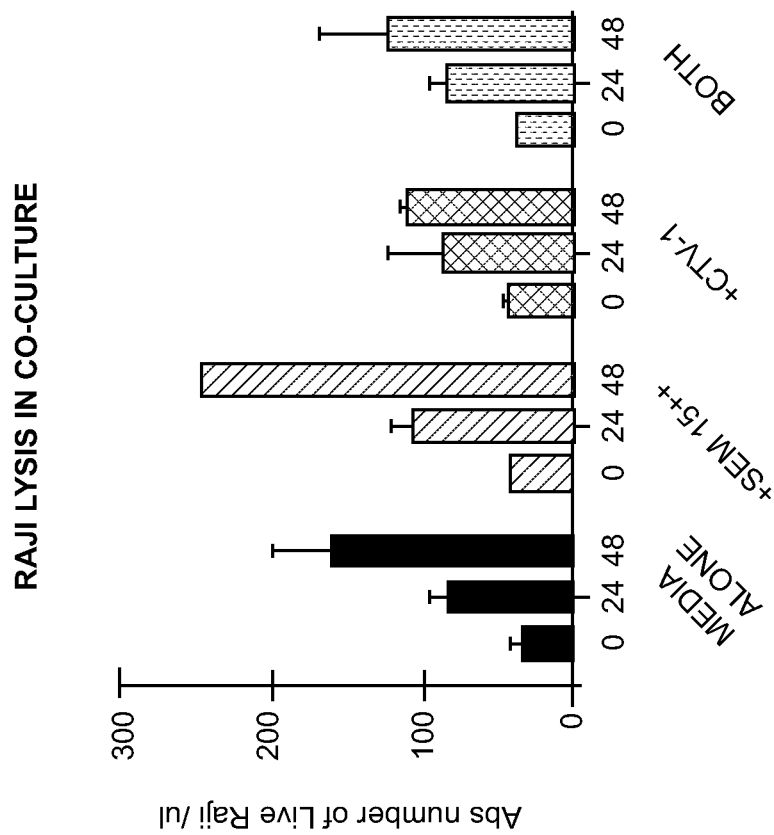
FIG. 2A shows only the addition of CTV1 cells, a tumor cell line that expresses Signal 1 and can prime NK cells can decrease the growth of RAJI cells, a NK resistant cell line, in a human PBMC culture.

By comparison, as demonstrated in FIG. 2B, the growth of the RAJI cells is increased if a CD15 positive SEM cells are added to the culture. Both the CTV1 and SEM cells are cancer cell lines. The difference between CTV1 cells and SEM cells is that CTV1 cells are a NK resistant cell line that expresses Signal 1 (priming signal) but has no Signal 2 (triggering signal). SEM cells are NK sensitive cells that express both Signal 1 and Signal 2. When CTV1 cells are added to the PBMC, the NK cells become primed and kill RAJI cells when they come in contact with them. The killing of the RAJI cells is demonstrated by decreased RAJI cell numbers (decreased growth). When SEM is added to the culture system, that NK cells kill the SEM cells. There is no killing of RAJI cells because there are no primed NK cells in the system. The increase in RAJI cell growth is likely to be due to the phenomenon of "cold target inhibition" where the small proportion of NK cells within the PBMC mix which are able to lyse RAJI cells spontaneously are preferentially targeting the SEM cells and reducing the number of cells able to target the RAJI cells.

Example 2: RAJI Lysis in Co-Culture Part II

Figure 3:
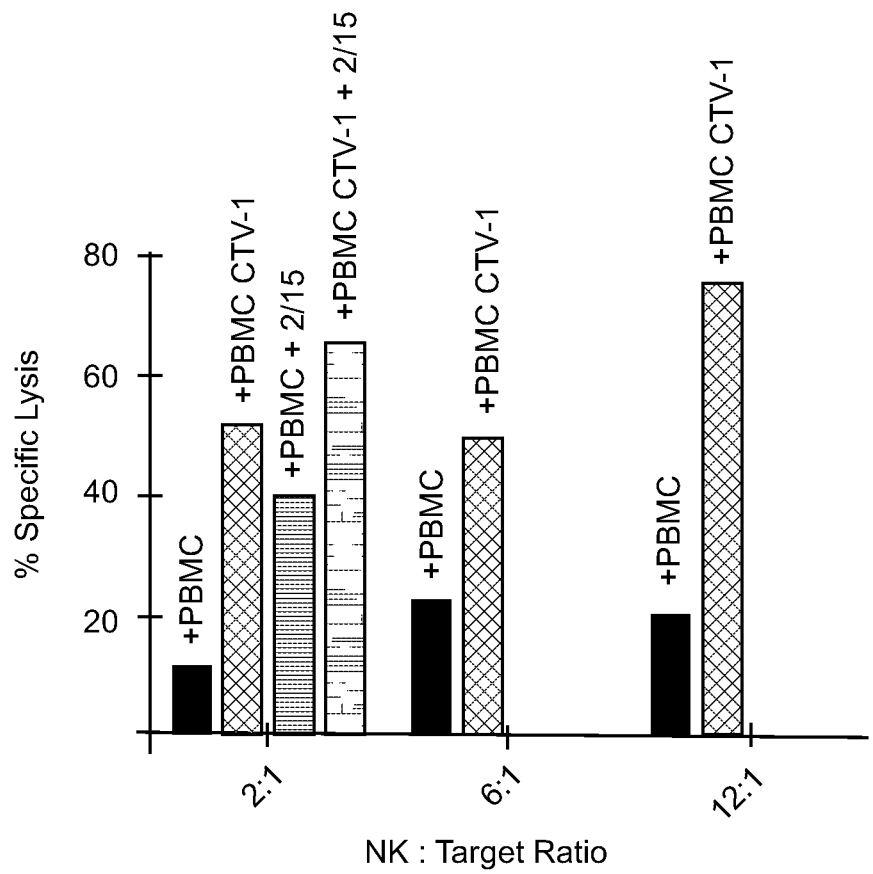
FIG. 3 shows that the decrease in growth of RAJI cells in the mixed culture is related to specific lysis RAJI by NK cells primed by the CTV1.

In a second experiment, we investigated the effects of each of: (i) PMBC alone; (ii) PBMC and CTV-1; (ii) PBMC with IL-2 and IL-15, and (iv) PBMC with a combination of CTV-1, IL-2 and IL-15, on the proliferation of RAJI cells. The results are shown in FIG. 3. Here, in addition to the above combinations, different ratios of NK cells to RAJI cells were investigated. We discovered that after forty-eight hours, and a ratio of about 12:1 PBMC to RAJI cells, the combination of PMBC and CTV-1 was much more effective in killing RAJI than PBMC alone. Even at a ratio of 2:1 PBMC to RAJI cells, the combination of PBMC plus CTV-1 was observably better than PBMC alone. Further, PBMC with CTV-1 showed higher lysis than PBMC with the combination low dose IL-2 and IL-15. However, the data illustrates that the combination of PBMC with CTV-1, and low dose IL-2 and IL-15 produced the greatest RAJI cell killing. While this experiment was performed in vitro, we believe that CTV-1, with or without IL-2 and IL-15, will be effective for in vivo priming of NK cells.

Furthermore, with the addition of minute quantities of inflammatory cytokines that promote NK cells function/health (IL2 and IL15), there is significantly more killing of the RAJI cells than with CTV1 cells alone or the cytokines alone.

FIG. 4 shows a method of treating cancer according to an embodiment.

While CTV-1 tumor cells are used throughout the instant disclosure, the invention is not intended to be limited to CTV-1 cells. The method may implement any tumor cells, or fragments thereof, which result in NK cell priming. Thus, a first tumor cell can be irradiated and introduced to a patient for in vivo priming of NK cells, and the primed NK cells can be subsequently presented to second tumor cells for lysing. These and other aspects of the invention will be appreciated by those having skill in the art.

We claim:
1. A method for treating cancer, comprising:
   administering to a patient having said cancer a priming tumor cell preparation for priming natural killer cells of the patient in vivo, the priming tumor cell preparation including:
      cells and/or membrane portions derived from a CTV-1 myeloid leukemia cell line,
      wherein the priming tumor cell preparation is inactivated to prevent proliferation thereof in the patient;
   whereby said patient is treated.
2. The method of claim 1, wherein the priming tumor cell preparation is irradiated to achieve inactivation.

* * * * *